(12) United States Patent  
Castro

(10) Patent No.: US 8,167,945 B1  
(45) Date of Patent: May 1, 2012

(54) DOUGHNUT-LIKE SPINAL IMPLANT

(75) Inventor: Frank Castro, Louisville, KY (US)

(73) Assignee: Cardinal Spine, LLC, Louisville, KY (US)

( * ) Notice: Subject to any disclaimer, the term of this patent is extended or adjusted under 35 U.S.C. 154(b) by 116 days.

(21) Appl. No.: 12/804,858

(22) Filed: Jul. 30, 2010

Related U.S. Application Data

(63) Continuation-in-part of application No. 12/381,955, filed on Mar. 18, 2009, now Pat. No. 8,075,620.

(51) Int. Cl.
*A61F 2/44* (2006.01)

(52) U.S. Cl. .............. 623/17.11; 623/17.16; 606/246; 606/249

(58) Field of Classification Search .......... 606/246–249, 606/279; 623/17.11–17.16
See application file for complete search history.

(56) References Cited

U.S. PATENT DOCUMENTS

| | | | |
|---|---|---|---|
| 6,146,421 A | 11/2000 | Gordon | |
| 6,228,118 B1 | 5/2001 | Gordon | |
| 6,425,920 B1 * | 7/2002 | Hamada | 623/17.16 |
| 6,533,818 B1 | 3/2003 | Weber et al. | |
| 7,018,412 B2 | 3/2006 | Ferreira et al. | |
| 7,025,787 B2 | 4/2006 | Bryan et al. | |
| 2005/0240271 A1 | 10/2005 | Zubok et al. | |
| 2008/0045952 A1 | 2/2008 | Kuslich | |
| 2009/0036987 A1 * | 2/2009 | Oh et al. | 623/17.16 |

OTHER PUBLICATIONS

Barack, R. L. Revision Totatl Hip Arthroplasty: The Femoral Component. J. Am Acad Orthop Surg 1995; 3(2); 79-85. USA.
Castro, F. P., Jr. Stingers, Cervical Cord Neurapraxia, and Stenois. Clin Sport Med 2003. 22: 483-492. USA.
Majd M.E., Vadhva, M., Holt R.T. Anterior Cervical Reconstruction Using Titanium Cages With Anterior Plating. Spine 1999; 24 (15): 1604-1610. USA.
Park J.B., Cho Y.S., Riew, K.D. Development of Adjacent-Level Ossification in Patient with an Anterior Cervical Plate. J. Bone Surg. 1005; 87-A: 558-563. USA, Mar. 2005.
Vertiflex—Print Advertisement for Octane A Spinal Implant System—Copyright 2008. USA.
Blackstone Medical Inc.—Print Advertisement for Pillar SA PEEK Spacer System—Copyright 2008. USA.
DePuy Spine Inc.—Print Advertisement for Spinal Implants—Copyright 2009. USA.
RSB Spine—Advertisement for Interplate C-P, C-PS and L-PS PEEK Spacers—Copyright 2009. USA.

* cited by examiner

*Primary Examiner* — Eduardo C Robert
*Assistant Examiner* — Christina Negrelli
(74) *Attorney, Agent, or Firm* — Kenneth F. Pearce

(57) ABSTRACT

A doughnut-like lumbosacral or intervertebral implant including an asymmetrical opening surrounded by a series of load-bearing curvatures. The doughnut-like implant can include a detachable connector. Preferred embodiments of the doughnut-like implant can include tapered lateral annular-like sides.

29 Claims, 11 Drawing Sheets

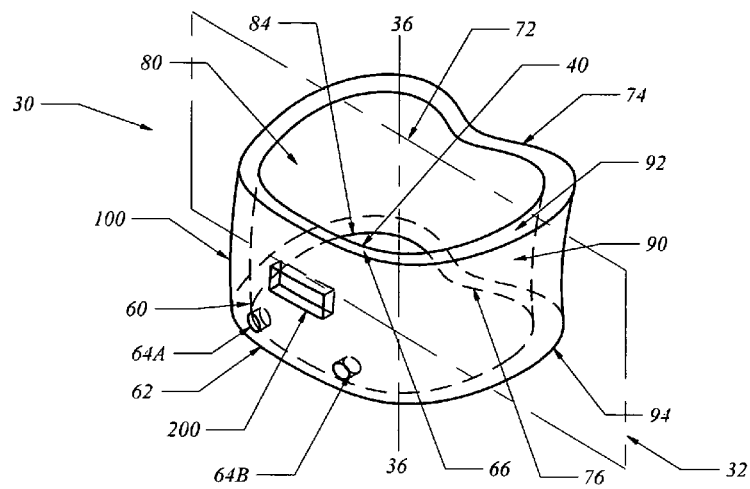
Fig. 1B
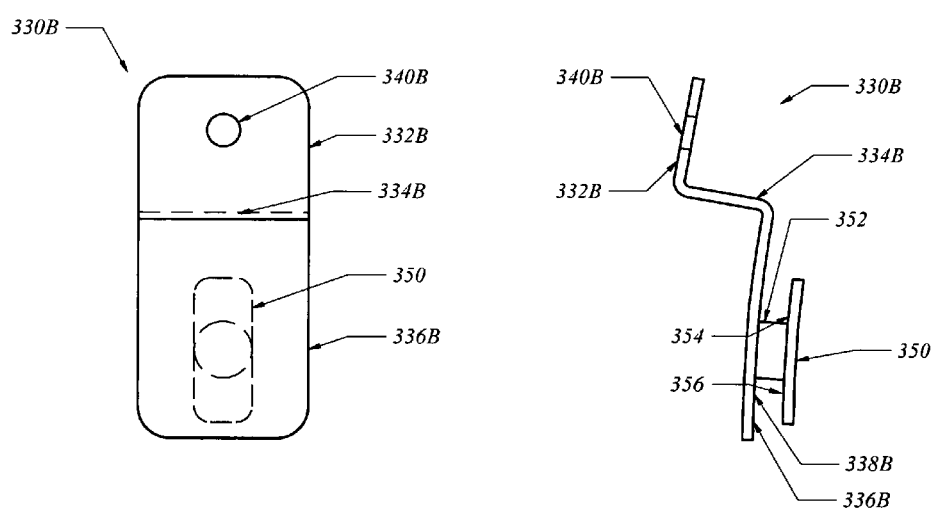
Fig. 2B
Fig. 3B

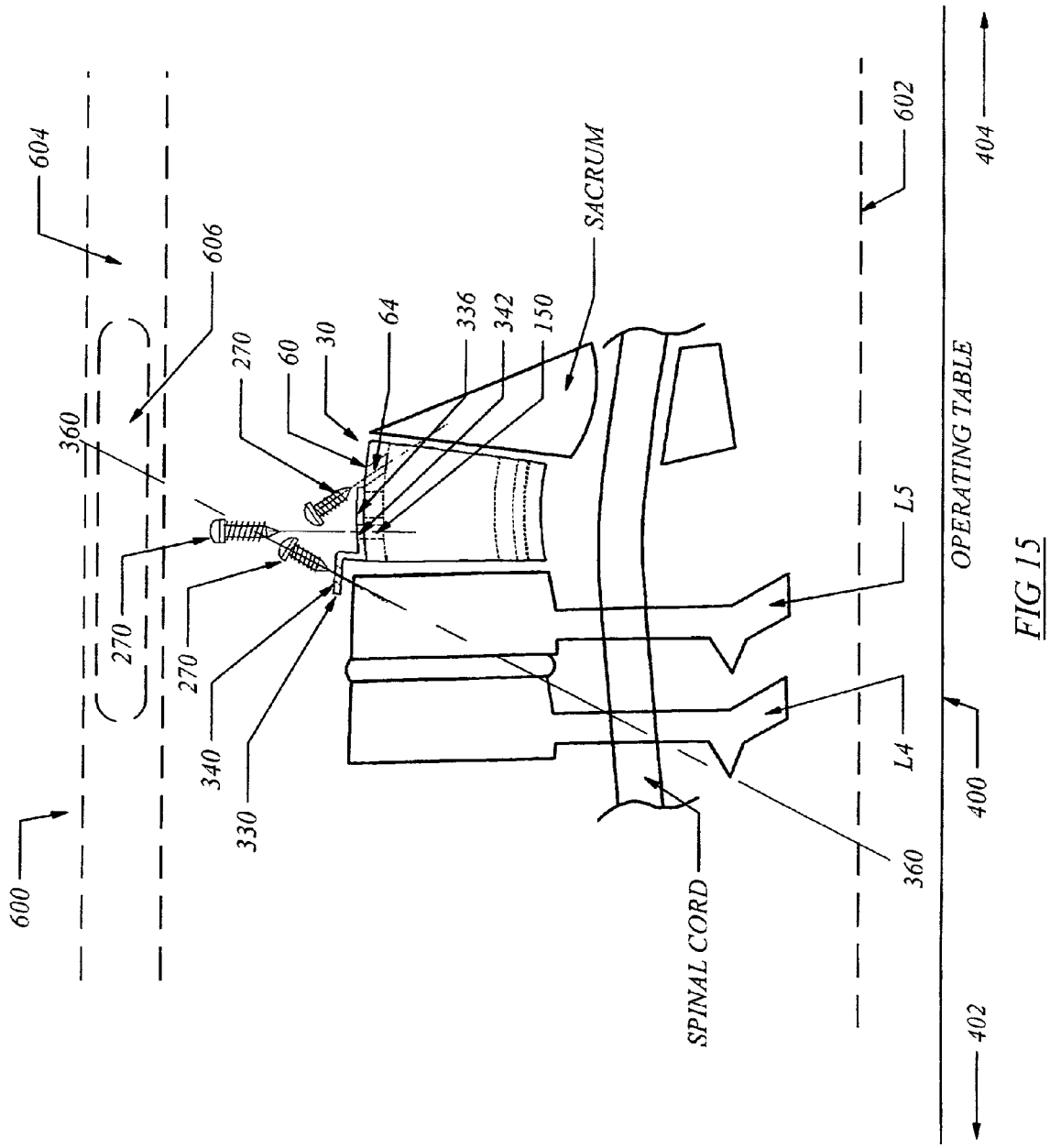

DOUGHNUT-LIKE SPINAL IMPLANT

This application is a Continuation-in-Part of Applications for U.S. patent Ser. No. 12/381,955 entitled—Doughnut-Like Spinal Implant—filed on Mar. 18, 2009 now U.S. Pat. No. 8,075,620.

BACKGROUND OF THE INVENTION

1. Field of the Invention

Among other things, the present invention is related to a lumbosacral or intervertebral implant. The doughnut-like implant includes an asymmetrical opening surrounded by a series of load-bearing curvatures. Preferred embodiments include one or more windows or apertures positioned in the load-bearing anterior curvature. Select preferred embodiments are provided with one or more detachable connectors. The detachable connectors include superior and inferior members that are offset from each other. Other preferred embodiments of the doughnut-like implant can include tapered lateral sections of the load-bearing curvatures. Still other preferred embodiments utilize a detachable connector that includes a keel extending therefrom.

2. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) U.S. Pat. No. 6,425,920—Hamada enables a spinal fusion implant. In part, Column 38 of Hamada reads, "Continuing with a description of the implant 701, FIG. 59 is a sectional view looking toward anterior end "A". Opposite the left side 713, a right side 715 is now seen. The implant 701 has a generally toroidal extent shaped mass of bone tissue 717. The central opening 707 may be packed with a material seen as material 718 which may be one of several combinations of materials and structures. Material 718 is also shown within the slot 709."

Among other things, the '920 Patent does not teach or suggest the use of an irregular central opening, an aperture located proximate the inferior edge for receiving a fastener, first and second annular-like sides distinct from the anterior and posterior curvatures, a posterior curvature protruding forward and toward the reference vertical axis, where the posterior curvature is angled more acutely than the anterior curvature, a forwardly extending arm attached to the superior edge of the anterior curvature and a plate comprising an aperture connected to the forwardly extending arm.

2) U.S. Pat. No. 6,146,421—Gordon enables a multiple axis intervertebral prosthesis. In part, Columns 3 and 4 of the '421 Patent read, "The present invention relates to a variable axis intervertebral disk prosthesis (see FIG. 1). The prosthesis has two components (see FIG. 4), male 10 and female 12, and is for implantation between two adjacent vertebrae in place of a spinal disk. Attachment to the adjacent vertebrae is accomplished at least in part by means of an attachment element, preferably mechanical attachment elements such as screws 14 which pass through a flange 16. Alternatives to screws such as pegs or posts are acceptable means for attaching the components to the vertebrae, as long as they are strong enough to handle the compressive forces exerted on it, and are a reliable form of fixation. Bone cement may also be used for attachment to the adjacent vertebrae, either in place of or in addition to mechanical attachment elements. The preferred length and diameter of the mechanical attachment elements is determined by the surgeon depending on the size of the patient and the location in the spine where the disk is being replaced. If using screws, they may be inserted straight into the vertebrae or at an angle. In one preferred embodiment, the screws are inserted straight into the vertebrae (see FIG. 1). In another preferred embodiment, a screw is inserted into the vertebra at an angle (see FIG. 5).

The male portion 10 of the prosthesis comprises a cylindrical support plate 18, which in a preferred embodiment is wedge shaped. The wedge shaped plate 18 allows for building lordosis into the prosthesis. The wedge shaped plate 18 has one rough-faced surface 20 that would mate with a vertebra. In a preferred embodiment, the male component 10 is the upper component and the rough surface 20 is on the upper surface 80 of the wedge shaped plate 18 (see FIG. 4). The rough surface allows for another means of fixation to a vertebra, as an alternative to or in addition to the mechanical attachment elements. A presently preferred embodiment has both attachment elements, such as screws 14, and a rough surface 20 to provide for the most stable fixation.

Extending vertically from the edge of the upper surface 20 of the support plate is at least one flange 16. In a preferred embodiment, the male component is the upper component and the flange extends upward from the thick side of the wedge shaped plate 28 (see FIG. 1). The flange is a mounting tab that can receive the attachment elements, such as screws 14. The screws are guided through openings 22 in the flange in order to attach the male portion 10 to a vertebra. There are at least two openings 22 through which (at least two) attachment elements can pass. In a preferred embodiment, the openings 22 in the flange 16 are figure eight shaped openings 34 (see FIG. 3). The figure eight shaped opening aids in facilitating different screw heights. Different heights are chosen by the surgeon depending on what best fits each particular patient. The opening 22 can also be circular, or oval in shape."

Among other things, the '421 Patent does not teach or suggest the use of doughnut-like implant with an irregular central opening, having a reference vertical axis, first and second annular-like sides distinct from the anterior and posterior curvatures, a posterior curvature protruding forward and toward the reference central vertical axis, where the posterior curvature is angled more acutely than the anterior curvature and a plate comprising an aperture, where the plate is connected with the forwardly extending arm, and where the plate extends upward from the forwardly extending arm and is generally parallel the reference axis.

3) U.S. Pat. No. 6,228,118—Gordon enables a multiple axis intervertebral prosthesis. The '118 Patent has identical disclosure as the '421 Patent's disclosure set forth above. Therefore, the '118 Patent does not teach or suggest the use of doughnut-like implant with an irregular central opening, having a reference vertical axis, first and second annular-like sides distinct from the anterior and posterior curvatures, a posterior curvature protruding forward and toward the reference central vertical axis, where the posterior curvature is angled more acutely than the anterior curvature and a plate comprising an aperture, where the plate is connected with the forwardly extending arm, and where the plate extends upward from the forwardly extending arm and is generally parallel the reference axis.

4) U.S. Pat. No. 6,533,818—Weber, et al. enables an artificial spinal disc. In part, Column 4 of the '818 Patent reads, "FIG. 1 shows a perspective view of one embodiment of the artificial spinal disc implant. The implant 10 is designed to approximate the shape and size of natural intervertebral discs. It has a planar top 12 and bottom 14 that bond to the vertebral bone when implanted in the vertebral spine. The implant is comprised of three distinct layers including a central layer 16."

Among other things, the '818 Patent does not teach or suggest the use of doughnut-like implant with an irregular central opening, having a reference vertical axis, a posterior curvature protruding forward and toward the reference vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature, a forwardly extending arm attached to the superior edge of the anterior curvature, and a plate comprising an aperture, where the plate is connected with the forwardly extending arm, and where the plate extends upward from the forwardly extending arm and is generally parallel the reference axis.

5) U.S. Pat. No. 7,018,412—Ferreira, et al. enables an allograft spinal implant. In part, Column 5 of the '412 Patent reads, "With reference to FIG. 5, a simplified lateral side view of an allograft spinal implant constructed according to the teachings of a second preferred embodiment of the present invention is generally identified at reference numeral 30. As with the first preferred embodiment, the implant is particularly intended for cervical spine applications. The implant 30 of the second preferred embodiment will be understood to be identical to the spinal implant 10 of the first preferred embodiment with the exception that superior and inferior end faces 32 and 34 of the implant 30 are not parallel to one another but relatively angled to accommodate natural spinal lordosis. In one exemplary application, the superior and inferior end faces 32 and 34 are angled from one another at approximately 5°. However, it is anticipated that the lordodic angle may fall within the range of 0° to approximately 10° or greater. The implant 30 includes an anterior height h 1, a posterior height h 2, an outer diameter or depth D, and a through hole 36 having a diameter d. As with the spinal implant 10 of the first preferred embodiment, the through hole diameter d of the implant 30 preferably ranges from 0 mm to approximately 6 mm and the overall diameter or depth D preferably ranges from approximately 8 mm to approximately 15 mm. In these applications, the anterior height preferably ranges from approximately 8 mm to approximately 14 mm and the posterior height ranges from approximately 5 mm to approximately 11 mm."

In part, Column 5 of the '412 Patent reads, "With reference to FIGS. 25-28, various stages of the implant 180 during a manufacturing process are illustrated. As shown in FIG. 25, a rough implant 121 is harvested from a transverse section of cortical bone. The rough implant 121 includes a through hole 122 that is naturally formed in the bone by the intramedullary canal."

In part, Column 8 of the '412 Patent reads, "With to FIGS. 45-48, an allograft spinal implant constructed in accordance with the teachings of a twelfth preferred embodiment of the present invention is illustrated and generally identified at reference character 250. The implant 250 is particularly intended for anterior lumbar interbody fusion applications. The long axis of the donor bone is indicated by arrow C. The implant 250 defines a generally central aperture 252. As with various prior embodiments of the present invention, the implant 250 is formed to include a plurality of concentric-arc ridges 254 on both the inferior and superior surfaces. In the embodiment illustrated, the superior and inferior end faces are angled from one another at approximately 6°. However, it is anticipated that the lordodic angle may fall within the range of 0° to approximately 6° or greater than 6°."

Among other things, the '412 Patent does not teach or suggest the use of a biocompatible metallic or plastic doughnut-like implant, a forwardly extending arm attached to the superior edge of the anterior curvature and a plate comprising an aperture, where the plate is connected with the forwardly extending arm, and where the plate extends upward from the forwardly extending arm and is generally parallel the reference axis.

6) U.S. Pat. No. 7,025,787—Bryan, et al. enables an implantable joint prosthesis and associated instrumentation. In part, Columns 11 and 12 of the '787 Patent read, "Preferably, shells 20, 40 are cup-like so as to include an outer convex surface 23 and an inner concave surface 21, 41. The outer surfaces 23 can be coated with a nonspherical sintered bead coating 22, 42, or with some other coating that will promote bony ingrowth. The inner surfaces 21, 41 (shown in FIG. 6) are preferably very smooth, and may be machined or polished.

The shells 20, 40 include a number of geometric features that as described in further detail below cooperate with other components of the devices. Specifically, these features include a central retaining post 27, 47, an outer circumferential groove 82, 84, and a radial stop or an extension 86, 88. The central retaining post 27, 47 extends axially from inner surfaces 21, 41. In addition, each shell 20, 40 includes an edge 73, 74, respectively. The outer circumferential grooves 82, 84 extend into the edges 73, 74 of the shells 20, 40. As seen best in FIG. 6, the radial stops or extensions 86, 88 extend from the edges 73, 74 in a direction generally perpendicular to the general plane of the shells 20, 40.

Each shell 20, 40 may also be provided with tabs or flanges 25, 45. The tabs or flanges 25, 45 extend from a portion of the edges 73, 74 in a direction generally perpendicular to the general plane of the shells 20, 40, but in a direction generally opposite the radial stops or extensions 86, 88. The tabs or flanges 25, 45 help to prevent long-term migration within the disc space, as well as catastrophic posterior expulsion, and the resulting damage to the spinal cord, other nerves, or vascular structures. The tabs or flanges 25, 45 may contain openings 26, 46 that can releasably engage an insertion tool (not shown). The insertion tool will generally contain flexible prongs to releasably engage openings 26, 46. The insertion tool will also generally include a disengagement block that can press against the side of the implant once it has been properly positioned in the intervertebral space and force the openings 26, 46 off of the prongs of the tool.

The shells 20, 40 can be made from any suitable biocompatible rigid material. In accordance with a preferred embodiment, the shells 20, 40 are made from a titanium alloy, and most preferably the titanium alloy is ASTM F-136. The bead coating 22, 42, however, is preferably made from ASTM F-67 pure titanium. As shown best in FIG. 7, central body 60 is preferably a donut-shaped structure, and includes a convex upper contact surface 94, a convex lower contact surface 96, and a central axial opening 98 formed through an inner surface 67 of the central body. In addition, central body member 60 preferably includes an upper shoulder 92 and a lower shoulder 90. Each shoulder 90, 92 consists of an indentation in the surface of the central body member which defines a ledge that extends around the circumference of the central body 60."

Among other things, the '787 Patent does not teach or suggest the use of doughnut-like implant with an irregular central opening, having a reference central vertical axis, an anterior curvature comprising an aperture located proximate the inferior edge for receiving a fastener, a posterior curvature protruding forward and toward the reference central vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature and a plate comprising an aperture, where the plate is connected with the forwardly extending arm, and where the plate extends upward from the forwardly extending arm and is generally parallel the reference axis.

7) US Pub. Patent App. No. 20050240271—Zubok, et al. discloses a cervical disc replacement. Paragraphs 44-46 of Zubok read, "Referring now to FIGS. 1-5, an artificial disc implant 100 of the present invention is shown in perspective, anterior, lateral, lateral cutaway, and posterior cutaway views, respectively. The implant 100 includes a first (e.g., upper) element 200 and a second (e.g., lower) element 300, each having an outwardly facing vertebral body contact surface 202, 302, and each having an inwardly facing articulation surface 204, 304. The elements 200, 300 are disposed as shown with the articulation surfaces 204, 304 nested against one another, and the vertebral body contact surfaces 202, 302 facing away from one another. When the implant 100 is disposed in an intervertebral disc space in a cervical spine, in this configuration and with the vertebral body contact surfaces 202, 302 engaged with respective adjacent vertebral body endplates (not shown), the implant 100 enables the adjacent vertebral bones to move relative to one another in accordance with proper anatomical motion, as further described below.

Preferably, at least one (and more preferably both) of the elements 200, 300 has at least one long-term fixation structure (e.g., flange 206, 306) having at least one feature (e.g., through hole 208 a, 208 b, 308) for securing the element to an adjacent vertebral body. For example, the upper element 200 has an anterior flange 206 that extends upwardly and has two through holes 208 a, 208 b, each of which accepts a bone screw (not shown). And, for example, the lower element 300 has an anterior flange 306 that extends downwardly and has one through hole 308 that accepts a bone screw (not shown). Once the elements 200, 300 are disposed in the intervertebral space with the vertebral body contact surfaces 202, 302 engaged with respective adjacent vertebral body endplates (not shown), securing of bone screws through the holes 208 a, 208 b, 308 and into the anterior surfaces of the adjacent vertebral bones helps prevent the elements from becoming dislodged from, or displaced in, the intervertebral space. Preferably, the bore axes of the through holes 208 a, 208 b, 308 are angled toward the adjacent vertebral body as shown.

Further preferably, at least one (and more preferably both) of the elements 200, 300 has at least one short-term fixation structure (e.g., spike 210 a, 210 b, 310 a, 310 b) for securing the element to an adjacent vertebral body (and more preferably to an adjacent vertebral body endplate). For example, each of the elements 200, 300 has a respective pair of outwardly directed spikes 210 a, 210 b, 310 a, 310 b. Once the elements 200, 300 are disposed in the intervertebral space with the vertebral body contact surfaces 202, 302 engaged with respective adjacent vertebral body endplates (not shown), the spikes 210 a, 210 b, 310 a, 310 b dig into the adjacent vertebral body endplates under the compression along the longitudinal axis of the spinal column, and thus help prevent the elements from becoming dislodged from, or displaced in, the intervertebral space. Preferably, each of the spikes 210 a, 210 b, 310 a, 310 b is sloped toward the vertebral body contact surface 202, 302 and toward the posterior direction on its posterior side as shown, to facilitate ease of insertion of the implant 100 into the intervertebral space, and is either perpendicular to the vertebral body contact surface 202, 302 on its anterior side (as shown) or sloped toward the vertebral body contact surface 202, 302 and toward the posterior direction on its anterior side (not shown), to help prevent the elements 200, 300 from anteriorly (or otherwise) slipping out of the intervertebral space."

Among other things, the '271 Application does not teach or suggest the use of doughnut-like implant with an irregular central opening, having a reference vertical axis, a posterior curvature protruding forward and toward the reference vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature and a plate comprising an aperture, where the plate is connected with the forwardly extending arm, and where the plate extends upward from the forwardly extending arm and is generally parallel the reference axis.

8) US Pub. Patent App. No. 20080045952—Kuslich discloses an annulus-reinforcing band. Paragraph 96 of Kuslich reads, "The band 12 is pliable and malleable before its interior space 14 (not shown in FIG. 2) is filled with the contents to be described. While in this initial condition, the band 12 may be passed, in a collapsed state, through a relatively small tube or portal, such as recited in U.S. Pat. Nos. 5,571,189 and 5,549,679, the entire contents of both references being incorporated herein by reference. This feature is important because access to the intervertebral disc is limited by anatomy and therefore safety considerations direct us to use the smallest possible portal of entry."

Among other things, the '952 Application does not teach or suggest the use of doughnut-like implant with an irregular central opening, having a reference vertical axis, a posterior curvature protruding forward and toward the reference vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature, a forwardly extending arm attached to the superior edge of the anterior curvature, and a plate comprising an aperture, where the plate is connected with the forwardly extending arm, and where the plate extends upward from the forwardly extending arm and is generally parallel the reference axis.

SUMMARY OF THE INVENTION

Unlike traditional spinal implants, the present invention provides is a doughnut-like spinal implant that is particularly well suited for implantation into the patient's lumbosacral region. The current doughnut-like spinal implant has an asymmetrical opening that can be filled with osteogenic substances, arthrodesis accelerating or other substances. Load-bearing annular-like sections of the current implant engage vertebra and resist spinal compression and gravitational forces.

An aspect of the present invention is to provide an embodiment of a doughnut-like implant that is particularly well suited for implantation into the patient's lumbosacral region.

Still another aspect of the present invention is to provide an embodiment of a doughnut-like implant that is manufactured of biocompatible metals, plastics or combinations thereof.

It is another aspect of the present invention to provide an embodiment of a doughnut-like implant that has distinct load bearing sections of load-bearing curvatures.

Yet another aspect of the present invention is to provide an embodiment of a doughnut-like implant that has sides that are tapered.

Yet still another aspect of the present invention is to provide an embodiment of an integral doughnut-like implant that has load-bearing sections of distinctive arcs.

It is still another aspect of the present invention to provide an embodiment of a doughnut-like implant that has a protruding anterior load-bearing curvature and a protruding load-bearing posterior curvature.

Still another aspect of the present invention is to provide an embodiment of a doughnut-like implant where the posterior load-bearing curvature is angled more acutely than the anterior load-bearing curvature.

It is another aspect of the present invention to provide an embodiment of a doughnut-like implant that has a forwardly protruding anterior curvature and a forwardly protruding posterior curvature.

Yet still another aspect of the present invention is to provide embodiment of a doughnut-like implant that has roughened upper and lower edges.

It is still another aspect of the present invention to provide an embodiment of a doughnut-like implant that a porous coating applied to at least part of the implant's upper or lower edges.

Still another aspect of the present invention is to provide an embodiment of a doughnut-like implant that has one or more windows.

Yet still another aspect of the present invention is to provide a detachable connector for covering at least a majority of the doughnut-like implant's window and deterring screws from backing out after insertion into bone.

It is still another aspect of the present invention to provide a detachable connector having first and second members offset from each other.

Still another aspect of the present invention is to provide an embodiment of a doughnut-like implant that has a superior cross-sectional area that is greater than the inferior cross-sectional area.

Yet still another aspect of the present invention is to provide a detachable connector having a member that is attachable to a vertebra.

It is still another aspect of the present invention to allow the surgeon to utilize standardized linear operating tools to secure the spinal implant between vertebra rather than requiring the use of specifically manufactured surgical tools with specialized angular contortions.

Still another aspect of the present invention is to provide a detachable connector having a keel extending therefrom.

An embodiment of the present invention can be described as a biocompatible metallic, plastic or combined metallic-plastic doughnut-like implant capable of frontal insertion between a superior and inferior lumbosacral vertebra, wherein the doughnut-like implant comprises a plurality of distinct generally upright load-supporting curvatures including load-bearing superior and inferior edges; the doughnut-like implant comprising: a) an asymmetrical central opening, including a central vertical axis, surrounded by the plurality of distinct generally upright load-supporting curvatures; b) an anterior load-supporting curvature protruding forward and away from the central vertical axis further comprising: i) one or more apertures located proximate the inferior edge for receiving one or more fasteners; ii) one or more windows allowing insertion of osteogenic, arthrodesis accelerating or other substances; and iii) a bore complementary to each window and proximate the superior edge; c) a posterior load-supporting curvature angled more acutely than the anterior member; d) a first lateral load-supporting curvature intermediate between and connected with the anterior and the posterior load-supporting curvatures, wherein superior and inferior edges of the first lateral load-supporting to curvature taper toward each other as the first lateral load-supporting-curvature traverses from the anterior load-supporting curvature to the posterior load-supporting curvature; e) a second lateral load-supporting curvature intermediate between and connected with the anterior and the posterior load-supporting curvatures, wherein superior and inferior edges of the second lateral load-supporting curvature taper toward each other as the second lateral load-supporting-curvature traverses from the anterior load-supporting curvature to the posterior load-supporting curvature; one or more detachable connectors associated with one or more windows; each detachable connector comprising: i) a first member including a hole for receiving a first fastener; ii) a second member capable of covering a majority of one of the windows for limiting outflow of the osteogenic, arthrodesis accelerating or other substances, wherein the second member comprises a hole for alignment with one of the bores and for receiving a second fastener; and iii) a transitional body connecting and offsetting the first member from the second member such that when said detachable connector is attached to the anterior load-supporting curvature the first member extends anterior to the anterior load-supporting curvature and superior to the anterior load-supporting curvature's superior edge; and g) a plurality of fasteners for use with the doughnut-like implant.

Another embodiment of the present invention can be described as a biocompatible doughnut-like implant capable of frontal insertion between a superior and an inferior vertebra; the doughnut-like implant comprising: a) an asymmetrical opening comprising a reference generally vertical axis; b) distinct load-bearing curvatures, including superior and inferior edges, forming the asymmetrical opening; the distinct load-bearing curvatures comprising: i) a first load-bearing curvature protruding forward and away from said reference axis, wherein the first load-bearing curvature further comprises: one to or more apertures located proximate the inferior edge for receiving one or more fasteners, one or more windows allowing insertion of osteogenic, arthrodesis accelerating or other substances and a bore complementary to each window and proximate the superior edge; ii) a second load-bearing curvature protruding toward the reference axis and angled more acutely than the first load-bearing curvature; iii) a third load-bearing curvature intermediate between and connected with the first load-bearing curvature and the second load-bearing curvature; iv) a fourth load-bearing curvature intermediate between and connected with the first load-bearing curvature and the second load-bearing curvature; c) a porous coating applied to one or more of the superior or inferior edges; and d) one or more detachable connectors associated with one or more windows.

Yet another embodiment of the present invention can be described as a biocompatible doughnut-like implant capable of frontal insertion between a superior and an inferior vertebra; the doughnut-like implant comprising an opening enclosed by a series of interconnected load-bearing generally upright sections including upper and lower edges and a detachable connector; the series further comprising: a) an anterior section protruding forwardly; the anterior section further comprising: i) one or more apertures located proximate the inferior edge; ii) at least one window allowing insertion of osteogenic, arthrodesis accelerating or other substances; and iii) a bore complementary with and superior to each window; b) a posterior section protruding forwardly and angled more acutely than the anterior section; c) first and second opposed lateral sections intermediate between and connected with the anterior and the posterior sections; and wherein the detachable connector is complementary with each window; the detachable connector further comprising: a) a first member including a first hole; and b) a second member including a second hole.

In still another embodiment, the present invention can be described as a biocompatible doughnut-like implant capable of frontal insertion between a superior and an inferior vertebra; the doughnut-like implant comprising: a) an opening enclosed by a series of interconnected load-bearing sections including upper and lower edges; the series comprising: i) an anterior section protruding forwardly; the anterior section further comprising: one or more apertures located proximate the inferior edge and one or more windows allowing insertion of osteogenic, arthrodesis accelerating or other substances; ii) a posterior section protruding forwardly and angled more acutely than the anterior section; and iii) first and second opposed lateral sections intermediate between and connected with the anterior and the posterior sections; b) a detachable connector complementary with at least one of the windows; the detachable connector further comprising: i) a first member including a first hole; ii) a second member including: a second hole or a keel; and c) one or more fasteners for use with the biocompatible doughnut-like implant.

Another embodiment of the present invention can be described as a detachable connector for use with a biocompatible spinal implant; the detachable connector comprising: a) a first member including a first hole for receiving a first fastener capable of securing the first member to bone; b) a second member capable of impeding outflow of osteogenic, arthrodesis accelerating or other substances from the biocompatible spinal implant, wherein the second member comprises: i) a second hole for receiving a second fastener capable securing the second member to the biocompatible spinal implant; or ii) a keel capable of securing the second member to the biocompatible spinal implant; and c) a transitional body connecting and offsetting the first member from the second member such that when said detachable connector is attached to the biocompatible spinal implant said first member extends anterior to the second member and superior to said biocompatible spinal implant.

Yet another embodiment of the present invention can be described as a detachable connector for use with a biocompatible spinal implant; the detachable connector comprising: a) a first member including a first hole for receiving a first fastener capable of securing the first member to bone; b) a second member capable of impeding outflow of osteogenic, arthrodesis accelerating or other substances from the biocompatible spinal implant, wherein the second member comprises: i) a second hole for receiving a second fastener capable securing the second member to the biocompatible spinal implant; or ii) a keel capable of securing the second member to the biocompatible spinal implant; and c) a transitional body connecting and offsetting the first member from the second member such that when the detachable connector is attached to the biocompatible spinal implant the first member extends anterior to the second member and superior to the biocompatible spinal implant.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 1B is a frontal perspective of an embodiment of the doughnut-like implant.

FIG. 2B is a frontal view of an embodiment of a detachable connector.

FIG. 3B is a lateral view of an embodiment of a detachable connector.

FIG. 15 is a representation of a midsection of a patient with the patient's right side of the patient cut away to expose a side view of the spinal cord, the sacrum and the lumbar 4 and 5 vertebras with the doughnut-like implant inserted between the lumbar 5 vertebra and the sacrum of the patient.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is an implant that can be inserted into a cavity of the spinal column. Surgical removal of tissue creates the cavity that can receive the implant. The doughnut-like implant includes an asymmetrical opening surrounded by distinct load bearing sections or curvatures that resist the compression associated with gravitational forces on the spinal column. Load bearing sections can be manufactured of biocompatible metals, plastics or combinations thereof, and preferred embodiments of the doughnut-like implant are manufactured of titanium, titanium alloys, stainless steel, non-resorbable and resorbable polymers. In the practice of select embodiments of the present invention, during surgical procedures, osteogenic substances, arthrodesis accelerating or other substances are placed into the asymmetrical opening. Select preferred embodiments of the current doughnut-like implant include one or more anterior windows, apertures, detachable connectors and/or bores for receiving fasteners. Other select preferred embodiments are provided with a detachable connector capable of covering a majority of an anterior window. Still other select preferred embodiments are provided with porous coating and/or roughened superior and inferior load-bearing edges.

The present doughnut-like implant is appropriate for implantation through the patient's frontal side. And it has been discovered that the doughnut-like implant is particularly well suited for insertion into the patient's lumbosacral region. Thus, the current doughnut-like implant meets the long felt but unfilled need of providing a unique load-bearing implant tailored for the patient's lumbosacral region that can be inserted through a frontal surgically created field anterior to the patient's lumbosacral region.

Figure 1:
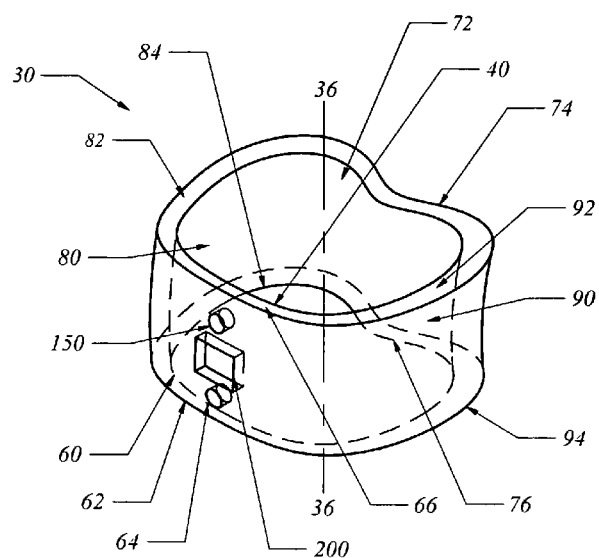
FIG. 1 is a frontal perspective of an embodiment of the doughnut-like implant.

FIG. 1 is a frontal perspective of an embodiment of doughnut-like implant (30) that has a reference central vertical axis (36-36). Asymmetrical opening (40) is formed by a series of four load-bearing curved sections or curvatures (60, 72, 80 and 90). Although not shown in FIG. 1, when engineering parameters require, asymmetrical opening (40) can be formed by more or less than four load-bearing curvatures.

Anterior curvature (60) protrudes forward and away from central vertical reference axis (36-36). Proximate the lower edge (62) of anterior curvature (60) is aperture (64). Proximate the upper edge (66) of anterior curvature (60) is bore (150). Fasteners (not shown in this view), such as screws or other devices acceptable in the art, can be inserted through aperture (64) to assist in securing doughnut-like implant (30) to vertebra (not shown in this view). In the preferred embodiment portrayed in FIG. 1, window (200) is positioned between bore (150) and aperture (64). Among other things, window (200) allows the surgical team to insert osteogenic substances, arthrodesis accelerating or other substances into doughnut-like implant (30) after implant (30) has been fitted into the surgically created cavity.

Posterior curvature (72) protrudes forward toward central vertical reference axis (36-36). Select preferred embodiments of doughnut-like implant (30) have posterior curvature (72) that is angled more acutely than anterior curvature (60). Curvature (72) can be acutely angled to prevent doughnut-like implant (30) from impinging on the spinal cord (not shown in this view) after doughnut-like implant (30) is insert between superior and inferior vertebra (not shown in this view). Posterior curvature (72) has upper edge (74) and lower edge (76).

Lateral curvature or annular-like side (80) of doughnut-like implant (30) is intermediate between anterior curvature (60) and posterior curvature (72). Lateral curvature or section (80) has upper boundary or edge (82) and lower boundary or edge (84). Annular-like side (80) is angled outwardly and away from central reference vertical axis (36-36).

Lateral curvature or annular-like side (90) of doughnut-like implant (30) is opposite annular-like side (80) of doughnut-like implant (30). Lateral section (90) is intermediate between anterior curvature (60) and posterior curvature (72). Lateral curvature or section (90) has upper boundary or edge (92) and lower boundary or edge (94). Annular-like side (90) is angled outwardly and away from central reference vertical axis (36-36).

Figure 2:
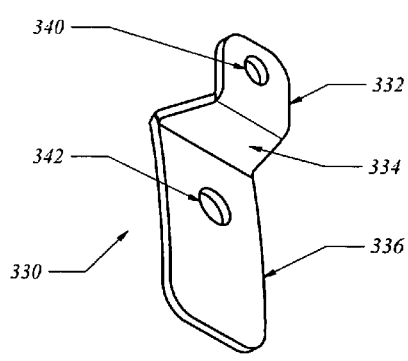
FIG. 2 is a frontal view of an embodiment of a detachable connector.

FIG. 2 is a frontal view of an embodiment of detachable connector (330). Detachable connector (330) has first member (332) including hole (340) for receiving a fastener (not shown in this view), transitional body (334) and second member (336) including hole (342) for receiving a fastener (not shown in this view). A fastener, such as a screw or other device acceptable in the art, inserted through hole (342) of second member (330) and bore (150) of anterior load-bearing curvature (60) can secure detachable connector (330) to doughnut-like implant (30). A fastener inserted through hole (340) can secure detachable connector (330) to vertebra. In select preferred embodiments, second member (336) of detachable connector (300) can be contoured such that when second member (336) is attached to anterior load-bearing curved section (60) of doughnut-like implant (30), the second member (336) follows the curvature of anterior load-bearing curved section (60) of doughnut-like implant (30).

Figure 3:
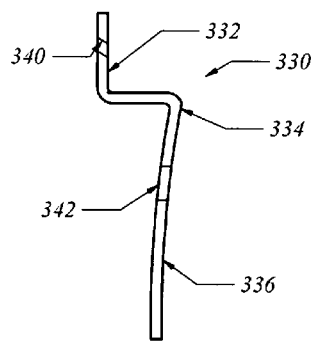
FIG. 3 is a lateral view of an embodiment of a detachable connector.

FIG. 3 is a lateral view of an embodiment of detachable connector (330). Transitional body (334) offsets first member (332) from second member (336). As shown in FIG. 3, hole (340) is angled upward, but in other embodiments hole (340) can be generally horizontal, i.e., similar to hole (342). In select embodiments, transitional body (330) is generally perpendicular to first member (332) and second member (336).

Figure 1A:
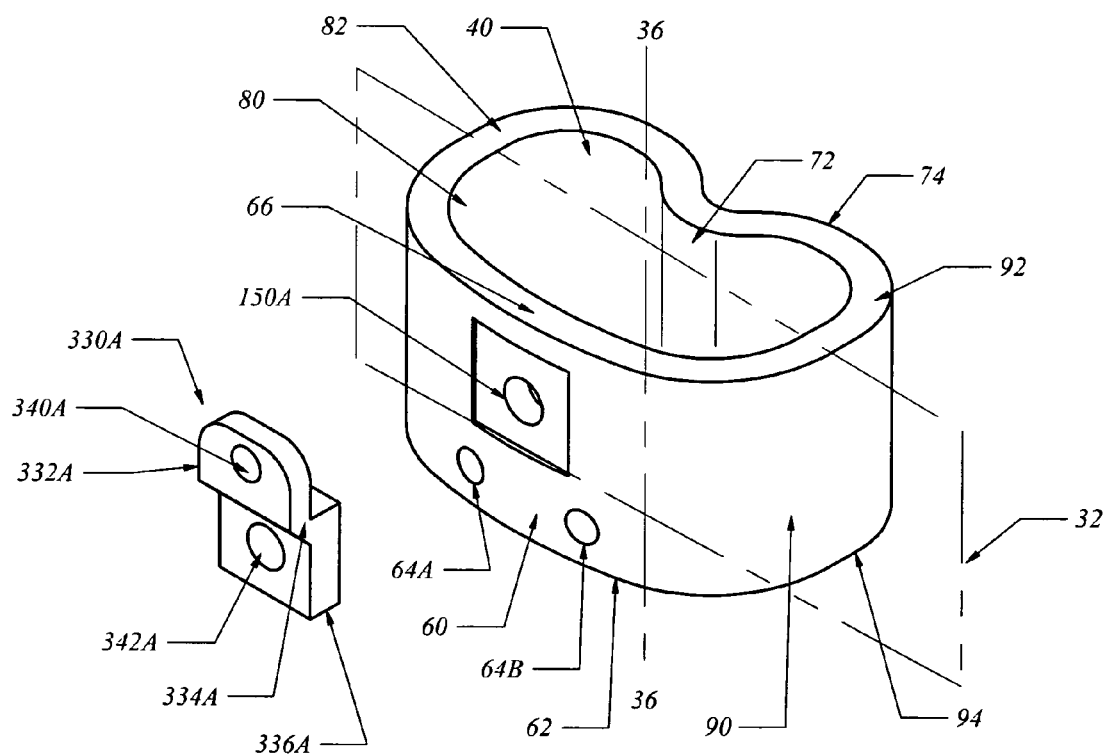
FIG. 1A is an exploded frontal perspective of an embodiment of the doughnut-like implant.

FIG. 1A is a frontal perspective of another embodiment of doughnut-like implant (30) that has a reference central vertical axis (36-36). Asymmetrical opening (40) is formed by a series of four load-bearing curved sections or curvatures (60, 72, 80 and 90). Although not shown in FIG. 1A, when engineering parameters require, asymmetrical opening (40) can be formed by more or less than four load-bearing curvatures.

Anterior curvature (60) protrudes forward and away from central vertical reference axis (36-36). Proximate the lower edge (62) of anterior curvature (60) are apertures (64A and 64B). Superior to apertures (64A and 64B) is bore (150A). By way of example, bore or window (150A) can have a diameter of about 6.5 millimeters. Surrounding bore or window (150A) is generally flat area (154) that is parallel to reference plane (32) bisecting lateral curvature (80) and lateral curvature (90). Generally flat area (154) is approximately 8 millimeters by 8 millimeters. Among other things, bore or window (150A) allows the surgical team to insert osteogenic substances, arthrodesis accelerating or other substances into doughnut-like implant (30) after implant (30) has been fitted into the surgically created cavity. Posterior curvature (72), lateral curvature or annular-like side (80) and lateral curvature or annular-like side (90) shown of doughnut-like implant shown in FIG. 1A are identical to corresponding structures disclosed in FIG. 1. Fasteners (not shown in this view), such as screws or other devices acceptable in the art, can be inserted through apertures (64A and 64B) to assist in securing doughnut-like implant (30) to vertebra (not shown in this view).

The preferred embodiment of spinal implant (30) enabled in FIG. 1A also includes detachable connector (330A). Detachable connector (330A) has first member (332A) including hole (340A) for receiving a fastener (not shown in this view), transitional body (334A) and second member (336A) including hole (342A) for receiving a fastener (not shown in this view). A fastener, such as a screw or other device acceptable in the art, inserted through hole (342A) of second member (336A) and bore or window (150A) of anterior load-bearing curvature (60) can secure detachable connector (330A) to doughnut-like implant (30). And a fastener inserted through hole (340A) of first member (332A) can secure detachable connector (330A) to vertebra.

As shown in FIG. 1A, hole (340A) is generally horizontal, but in other embodiments hole (340A) can be angled upward. Although not shown in FIG. 1A, in some preferred embodiments, transitional body (334A) can be generally perpendicular to first member (332A) and second member (336A).

FIG. 1B is a frontal perspective of another embodiment of doughnut-like implant (30) that has a reference central vertical axis (36-36). Asymmetrical opening (40) is formed by a series of four load-bearing curved sections or curvatures (60, 72, 80 and 90). Although not shown in FIG. 1B, when engineering parameters require, asymmetrical opening (40) can be formed by more or less than four load-bearing curvatures.

Anterior curvature (60) protrudes forward and away from central vertical reference axis (36-36). Proximate the lower edge (62) of anterior curvature (60) are apertures (64A and 64B). Superior to apertures (64A and 64B) is window (200). Among other things, window (200) allows the surgical team to insert osteogenic substances, arthrodesis accelerating or other substances into doughnut-like implant (30) after implant (30) has been fitted into the surgically created cavity. Although not shown in FIG. 1B, doughnut-like spinal implant (30) can include a generally flat area similar to the generally flat area (154) shown in FIG. 1A. Posterior curvature (72), lateral curvature or annular-like side (80) and lateral curvature or annular-like side (90) shown of doughnut-like implant shown in FIG. 1A are identical to corresponding structures disclosed in FIG. 1. Fasteners (not shown in this view), such as screws or other devices acceptable in the art, can be inserted through apertures (64A and 64B) to assist in securing doughnut-like implant (30) to vertebra (not shown in this view).

FIG. 2B is a frontal view of an embodiment of detachable connector (330B). Detachable connector (330B) has first member (332B) including hole (340B) for receiving a fastener (not shown in this view), transitional body (334B) and second member (336B) including keel (350) extending away from second member (336B). Insertion of keel (350) through window (200) and subsequent rotation of keel (350) secures detachable connector (330B) to doughnut-like implant (30).

FIG. 3B is a lateral view of an embodiment of detachable connector (330B). Transitional body (334B) offsets first member (332B) from second member (336B). As shown in FIG. 3A, hole (340B) is generally horizontal, but in other embodiments hole (340B) can be angled upward. In select embodiments, transitional body (330B) is generally perpendicular to first member (332B) and second member (336B). Arm (352) is generally perpendicular to second member (336B) and extends keel (350) away from outer edge (338B) of second member (336B). Keel (350) and detachable connector (330B) are manufactured to such dimensions that keel (350) can be inserted through window (200), and upon subsequent rotation detachable connector (330B), inner edges (354 and 356) of keel (350) and outer edge (338B) of second member (336B) secure detachable connector (330B) to doughnut-like implant (30). In select preferred embodiments, detachable connector (330B) is a mono-bloc construction.

Figure 4:
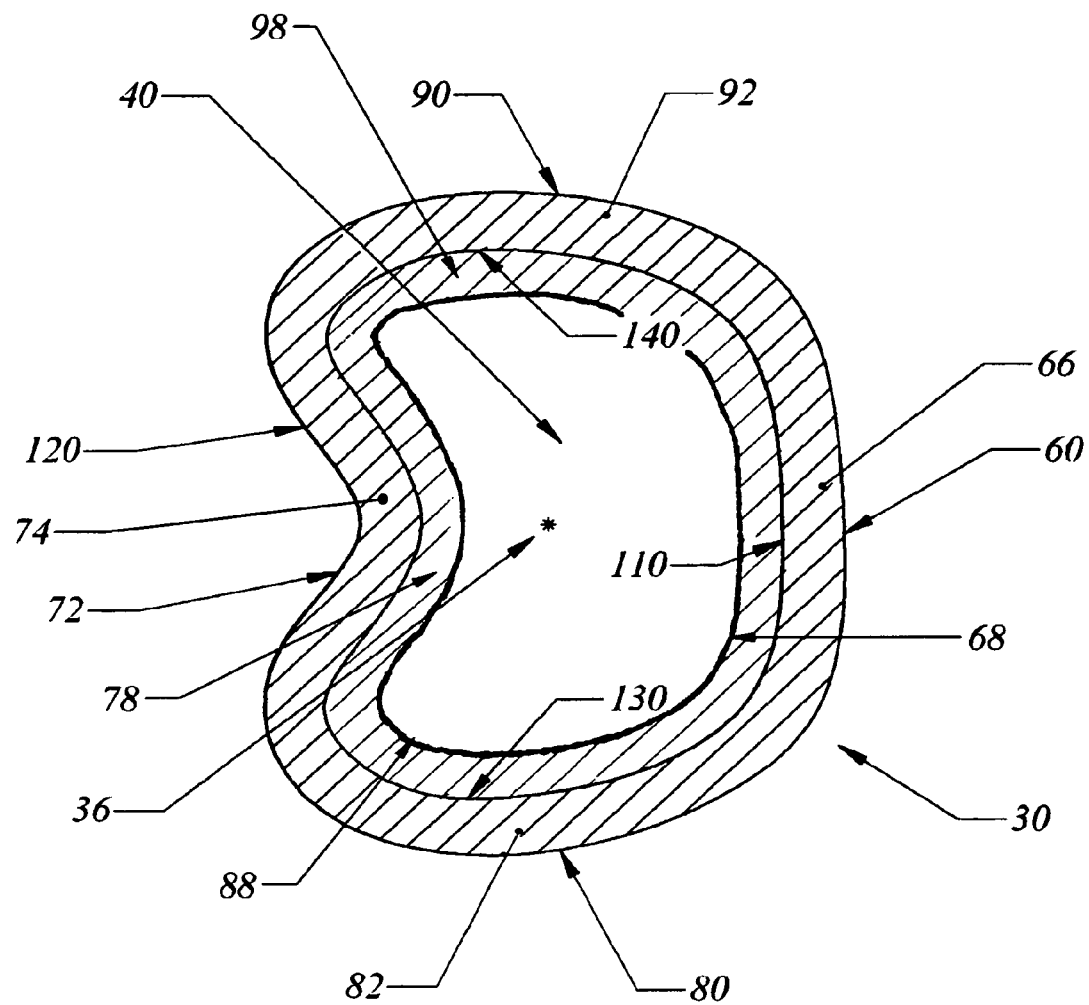
FIG. 4 is a top plan view of an embodiment of doughnut-like implant.
Figure 5:
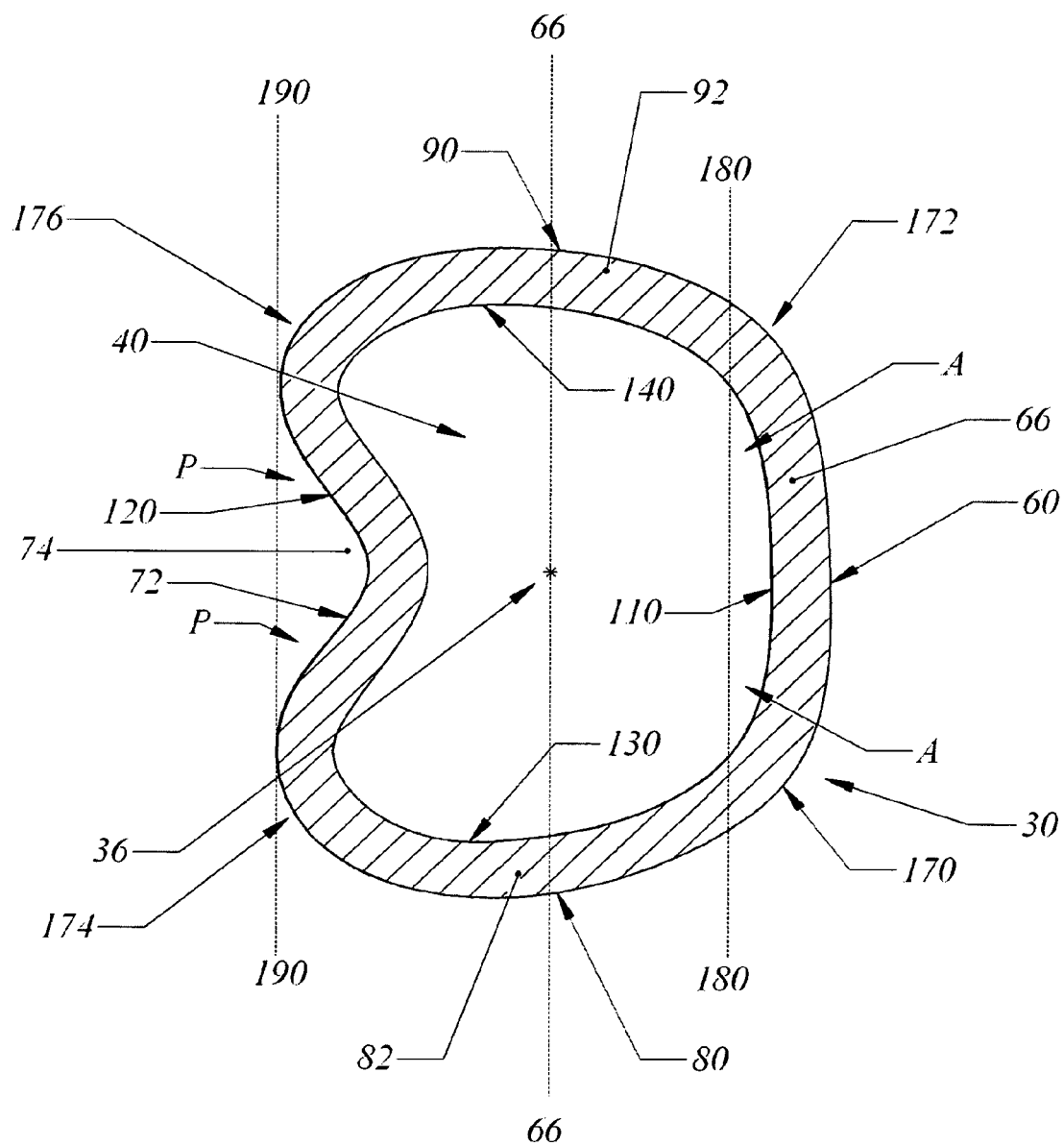
FIG. 5 is a top plan view of an embodiment of doughnut-like implant.

FIGS. 4 and 5 are top plan views of embodiments of doughnut-like implant (30). Asymmetrical opening (40) is surrounded by anterior section (60), posterior section (72) and lateral sections (80 and 90). Upper edges (66, 74, 82 and 92) of sections (60, 72, 80 and 90) are shown. In select preferred embodiments of the current invention, the edges of load-bearing curvatures are integral with each other.

As shown in FIG. 4, tapered wall (68) of anterior section (60), tapered wall (78) of posterior section (72) and tapered wall (88) of lateral section (80) and tapered wall (98) of lateral section (90) enable a tapered embodiment of doughnut-like implant (30). In the embodiment portrayed in FIG. 4, from the superior side to inferior side of doughnut-like implant (30), walls (68), (78), (88) and (98) are tapered inwardly such that the superior cross-sectional area as measured along the upper edges (66, 74, 82 and 92) is greater than the inferior cross-sectional area associated with the lower edges of walls (68), (78), (88) and (98).

With reference to FIGS. 4 and 5, load-bearing section (60) has bend (110). Load-bearing section (72) is provided with bend (120). And load-bearing sections (80 and 90), respectively have bends (130 and 140). In select preferred embodiments of the current invention, each bend's arc (110, 120, 130 and 140) is distinct from its adjacent bend's arc (110, 120, 130 and 140).

In preferred embodiments of the present invention, bend (120) of posterior section (72) is angled to protrude more acutely toward central vertical reference axis (36-36) than bend (110) of anterior section (60) is angled to protrude away from reference axis (36-36). For select preferred embodiments, posterior section (72) is angled to prevent doughnut-like implant (30) from impinging on the spinal cord (not shown in this view). Depending on engineering parameters, bends (130 and 140) of lateral sections (80 and 90) are similar or identical.

As used herein, anterior vertical reference plane (180-180) extends between intersection (170) of bend (130) and bend (110) and intersection (172) of bend (140) and bend (110). An anterior protrusion angle (A) is measured from the intersection of anterior vertical reference plane (180-180) and curvature (110). Preferred embodiments of the current invention practice doughnut-like implants (30) with anterior protrusion angles (A) of about 30 degrees or less.

As used herein, posterior vertical reference plane (190-190) extends between intersection (174) of bend (130) and bend (120) and intersection (176) of bend (140) and bend (120). A posterior protrusion angle (P) is measured from the intersection of anterior vertical reference plane (190-190) and bend (120). Preferred embodiments of the current invention practice doughnut-like implants (30) with posterior protrusion angles (P) of more than 30 degrees. Depending on predetermined engineering parameters, anterior vertical reference plane (180-180) and posterior vertical reference plane (190-190) can be parallel with each other.

Figure 6:
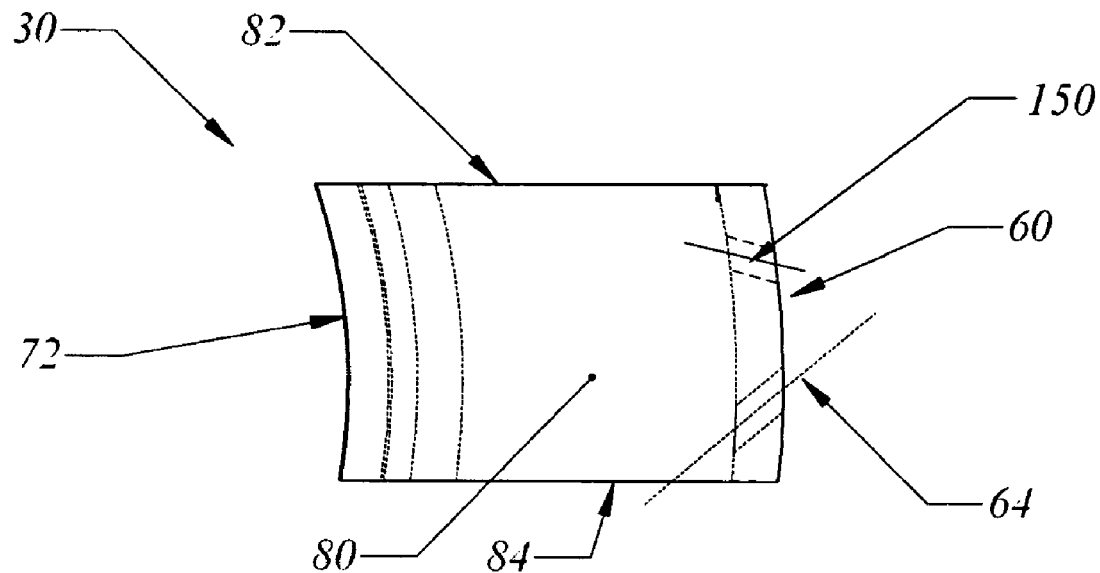
FIG. 6 is a lateral representation of an embodiment of doughnut-like implant.

With the view centered on the outward side of annular-like side (80), FIG. 6 is a lateral representation of an embodiment of doughnut-like implant (30). Aperture (64) (shown in phantom) is angled downward and bore (150) is generally horizontal. Upper edge (82) and lower edge (84) of annular-like side (80) follow the same arc.

Figure 7:
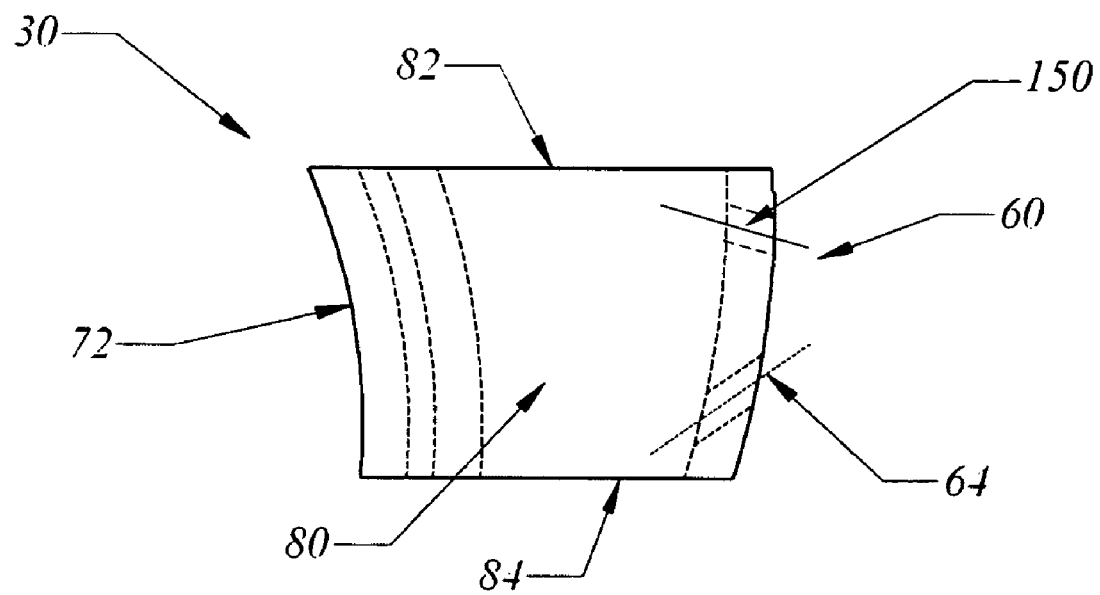
FIG. 7 is a lateral representation of an embodiment of doughnut-like implant.

FIG. 7 is a lateral representation of doughnut-like implant (30) where arc of edge (82) of doughnut-like implant (30) encompasses a greater area than arc of edge (84) of doughnut-like implant (30). In the embodiment portrayed in 7, anterior load-bearing section (60), posterior load-bearing section (72) and lateral load-bearing sections (80 and 90) are tapered between superior and inferior edges (82 and 84) of doughnut-like implant (30). By way of illustration, from the superior side to inferior side of doughnut-like implant (30), load bearing sections (60, 72, 80 and 90) are tapered inwardly such that the superior cross-sectional area as measured along the superior periphery of load bearing sections (60, 72, 80 and 90) is greater than the inferior cross-sectional area as measured along the inferior periphery of load bearing sections (60, 72, 80 and 90).

Figure 8:
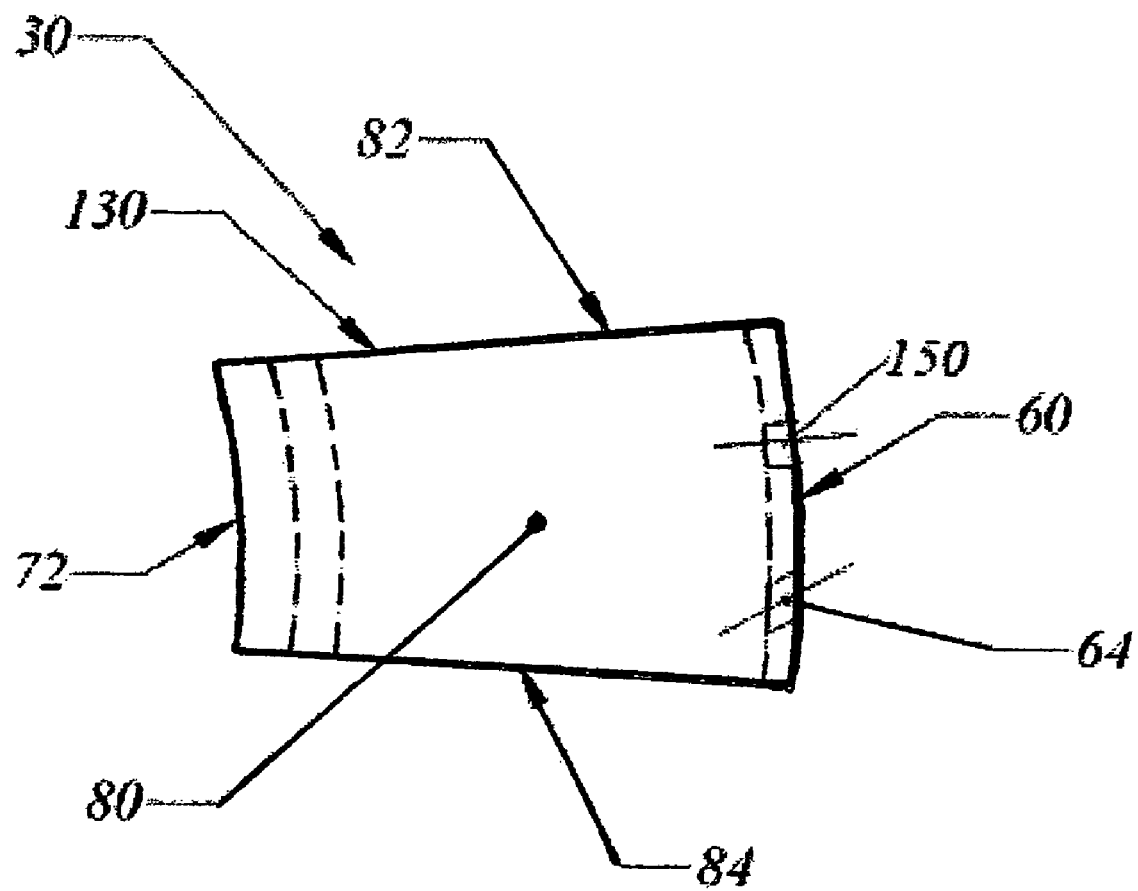
FIG. 8 is a lateral representation of an embodiment of doughnut-like implant.

With the view centered on the outward side of annular-like side (80), FIG. 8 is a lateral representation of a preferred embodiment of doughnut-like implant (30). Aperture (64) (shown in phantom) is angled downward and bore (150) (shown in phantom) is generally horizontal. Upper edge (82) and lower edge (84) of curvature (80) are tapered. In select preferred embodiments, upper boundary (82) and lower boundary of annular-like side (80) taper toward each other as bend (130) traverses from anterior curved section (60) to posterior curved section (72). Although not shown in FIG. 8, in similar manner, annular-like side (90) can taper from anterior curved section (60) to posterior curved section (72).

Figure 9:
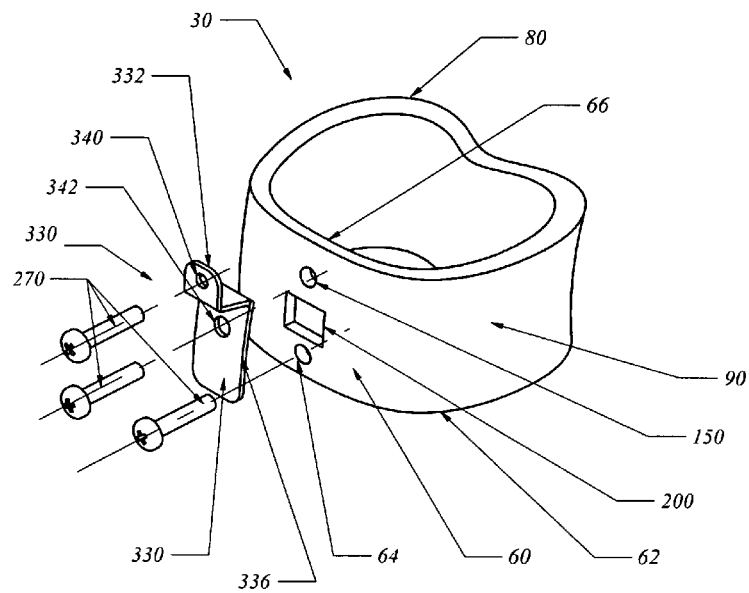
FIG. 9 is an exploded perspective of another embodiment of doughnut-like implant.

FIG. 9 is an exploded perspective of another embodiment of doughnut-like implant (30) and detachable connector (330). Anterior load-bearing curvature (60) has lower edge (62), upper edge (66) and window (200) that is positioned between aperture (64) proximate lower edge (62) and bore (150) proximate upper edge (66). In select preferred embodiments, superior edge (66) and inferior edge (62) of anterior load-bearing curvature (60) taper apart from each other as superior edge (66) and inferior edge (62) traverse from the center of anterior load-bearing curvature (60) toward lateral load-bearing curvature (80) and lateral load-bearing curvature (90), respectively.

First fastener (270) insertable through hole (342) and bore (150) secures second member (336) of detachable connector (330) to anterior load-bearing curvature (60) of doughnut-like implant (30). Second fastener (270) insertable through hole (340) can secure first member (332) of detachable connector (330) to vertebra (not shown in this view). When attached to doughnut-like implant (30), second member (336) of detachable connector (330) covers all or a majority of window (200).

Figure 10:
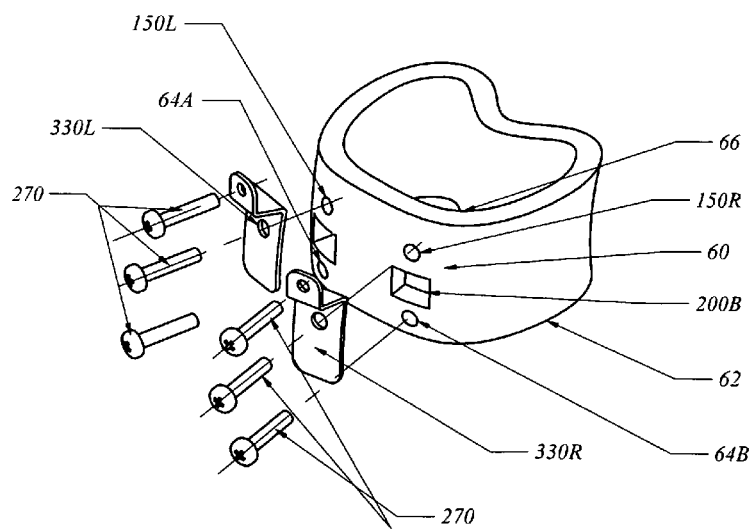
FIG. 10 is an exploded perspective of another embodiment of doughnut-like implant.

As shown in the FIG. 10 preferred embodiment, windows (200A and 200B) are positioned between apertures (64A and 64B) and bores (150L and 150R) and anterior curvature (60) of doughnut-like implant (30). The embodiment enabled in FIG. 10 is similar to the embodiment portrayed in FIG. 9 and fasteners (270) secure detachable connectors (330L and 330R) to doughnut-like implant (30) and vertebra (not shown in this view). Although not shown in FIGS. 9 and 10, detachable connectors (330A) and (330B) enabled in FIGS. 1A and 1B can also be utilized with windows (200A) or (200B).

Figures 11, 12, 13:
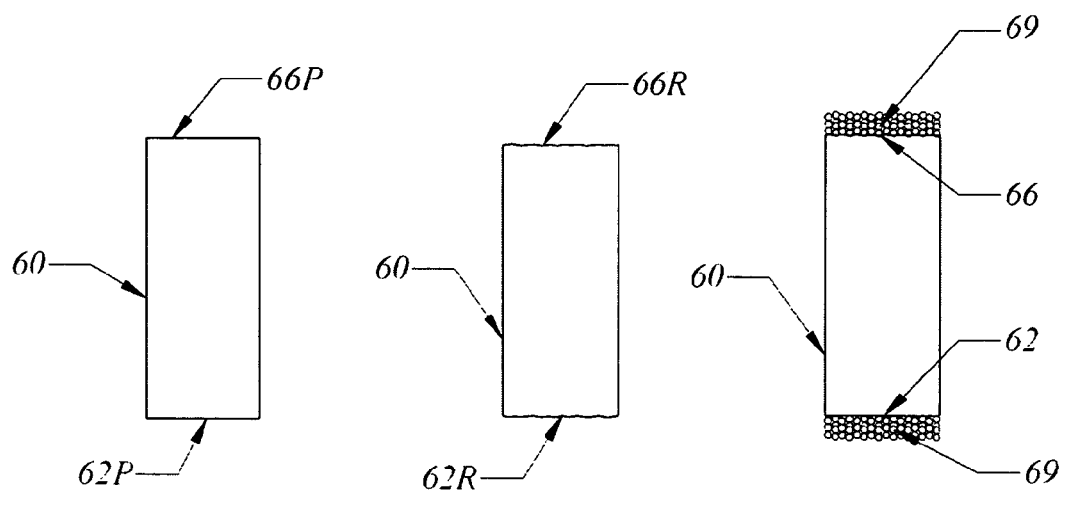
FIG. 11 is a cross-sectional view of an embodiment of anterior curved section.
FIG. 12 is a cross-sectional view of an embodiment of anterior curved section.
FIG. 13 is a cross-sectional view of an embodiment of anterior curved section.

FIG. 11 is a cross-sectional view of an embodiment of anterior curved section (60). In select embodiments, upper edge (66P) is polished and lower edge (62P) is also polished. Although not shown in FIG. 11, upper edge (74) and lower edge (76) of posterior curvature (72) and upper edges (82 and 92) and lower edges (84 and 94) of lateral curvatures (80 and 90) can be polished.

FIG. 12 is a cross-sectional view of an embodiment of anterior curved section (60). In select embodiments, upper edge (66R) is roughened and lower edge (62R) is also roughened. Although not shown in FIG. 12, upper edge (74) and lower edge (76) of posterior curvature (72) and upper edges (82 and 92) and lower edges (84 and 94) of lateral curvatures (80 and 90) can be roughened.

FIG. 13 is a cross-sectional view of an embodiment of anterior curved section (60). In select embodiments, porous coating (69) is attached to upper edge (66) and lower edge (62) of anterior curved section (60). Porous coating (69) can be a biocompatible polymeric layer, ranging from about 1 millimeter to about 2 millimeters in thickness. It is believed that the porous coating enhances bone ingrowth and improves stability of the doughnut-like spinal implant. Although not shown in FIG. 13, upper edge (74) and lower edge (76) of posterior curvature (72) and upper edges (82 and 92) and lower edges (84 and 94) of lateral curvatures (80 and 90) can also be provided with a porous coating to enhance bone ingrowth. Depending on engineering parameters, porous coating (69) can be applied to either polished or roughened edges of the doughnut-like implant.

Figure 14:
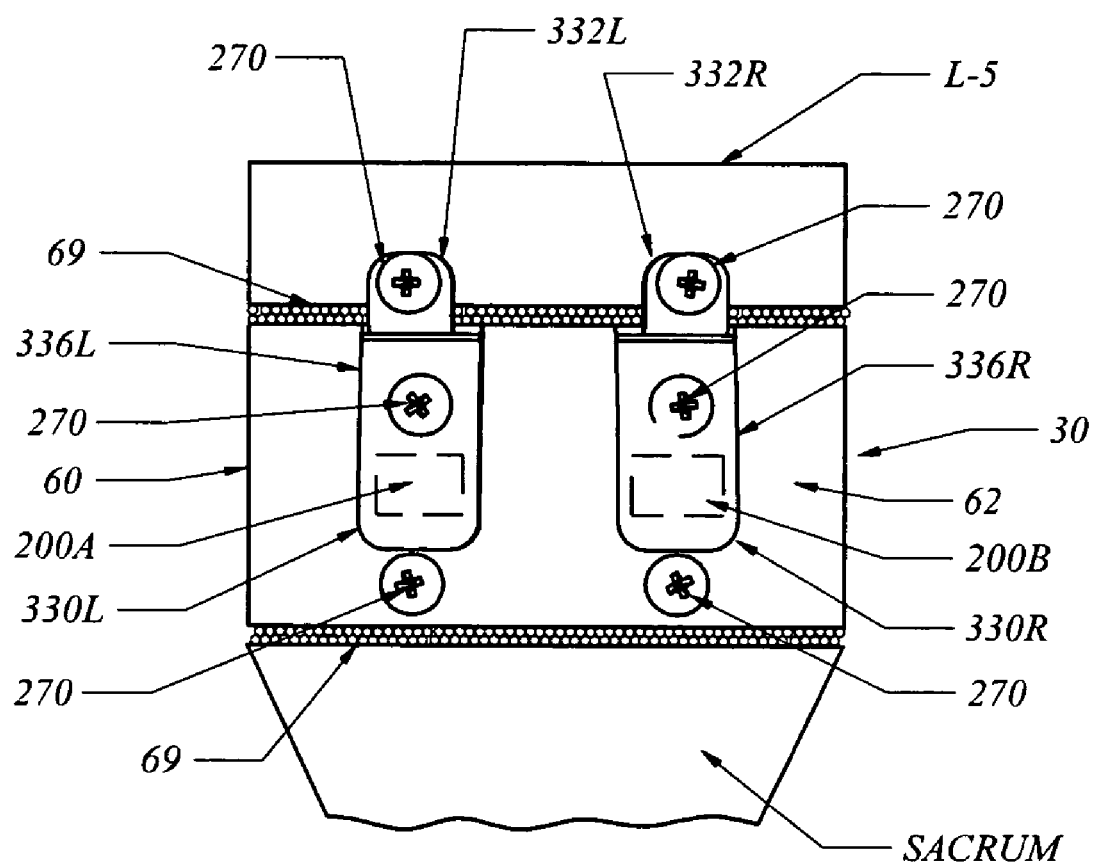
FIG. 14 is frontal view of an embodiment of doughnut-like implant.

FIG. 14 is frontal view of a preferred embodiment of doughnut-like implant (30) that is secured between the lumbar 5 vertebra and the sacrum. First upper fasteners (270) secure first member (332L) of detachable connector (330L) to the L-5 vertebra and first member (332R) of detachable connector (330R) to the L-5 vertebra. Porous coating (69) has been applied to upper edge (66) and lower edge (62) of anterior load-bearing curvature (30). Window (200A) is covered by second member (336L) of detachable connector (330L) and window (200B) is covered by second member (336R) of detachable connector (330R). Intermediate fasteners (270) secure second members (336L and 336R) of detachable connectors (330L and 330R) to anterior load-bearing curvature (60). Lower fasteners (270) assist in further securing doughnut-like implant (30) to the sacrum.

FIG. 15 is a representation of a midsection of patient (600) with the patient's right side of the patient cut away to expose a side view of the spinal cord, the sacrum and the lumbar 4 and 5 vertebras with doughnut-like implant (30) inserted between the lumbar 5 vertebra and the sacrum of patient (600). At least a portion of the patient's (600) backside (602) rests on horizontal operating table (400). Operating table (400) has head (402) for supporting patient's (600) head and foot (404) for supporting patient's (600) feet. Patient also has front side (604) and incision (606) on front side of patient (600) for allowing doughnut-like spinal implant (30) to be inserted into patient (600).

As shown in FIG. 15, screw (270) is inserted through hole (340) of first member (332) of detachable connector (330) into the lumbar 5 vertebra. Fastener (270) is inserted through hole (342) and bore (150) to secure second member (336) of detachable connector (330) to anterior load-bearing section (60) of doughnut-like implant (30). Screw (270) is inserted through aperture (64) of anterior load-bearing section (60) of doughnut-like implant (30) and into the sacrum.

In select preferred embodiments, as measured from the outward side of first member (332) to the inward side of first member (332), hole (340) of first member (332) can be angled toward the patient's head, and as measured from the outward side to the inward side of anterior load-bearing section (60), aperture (64) of anterior load-bearing section (60) can be angled toward the patient's feet. The angling of hole (340) and aperture (64) enhances the load bearing capacity of doughnut-like implants (30) as well reducing the likelihood that screws will back out of the vertebra as the spinal column is subjected to movement and gravitational forces. Additionally, the angling of hole (340) and aperture (64) allows the use of fasteners of greater length which also can improve the stability of the doughnut-like implant (30).

It is believed that prior to the present invention specialized surgical tools having angular bends were needed to attach screws to bone to secure implants between the L5 vertebra and the sacrum. Such tools with angular bends, e.g., screw drivers, increased the difficulty of securing the screws to bone as well as the risk of damaging tissue surrounding the surgical field. The current doughnut-like spinal implant (30) can eliminate the need for using angular or bent specialized screw drivers to secure screws to bone. In short, commercial-off-the-shelf surgical linear screw drivers can be used to the secure the current invention between the L5 lumbar vertebra and the sacrum—improving the secure fit between screw and bone as well as reducing the risk of damaging tissue, such as the femoral arteries, associated with the surgical field.

The present doughnut-like spinal implant (30) allows the surgeon to utilize an operating angle (OA) more conducive to the use of linear surgical instruments than previously used when inserting a screw through the doughnut-like lumbosacral implant into the L5 lumbar vertebra. In the practice of the present invention, depending on the location of patient's (600) vertebra and the patient's (600) girth, the operating angle (OA) can vary from about 45 degrees to about 110 degrees. It has been discovered such operating angles allow the use of standardized linear operating tools or instruments. For the purposes of the preferred embodiment enabled in FIG. 15, the operating angle (OA) is measured by the intersection of the concentric longitudinal axis (360-360) of hole (340) and operating table (400) where the operating angle (OA) is further defined by the arc degrees from the foot (404) side of operating table to concentric longitudinal axis (360-360). The operating angles (OA) of other detachable connectors enabled in this application but not shown in FIG. 15 are also measured by utilizing the intersections of the concentric longitudinal axis of holes (340A) or (340B) and operating table (400).

The present doughnut-like spinal implant (30) facilitates the insertion of a fixation screw into the L5 vertebra with increased ease and safety. As previously indicated, operating angles (OA) associated with the practice of the present invention allow the use of linear surgical instruments. Elimination of flexible or multiaxial tools reduces the risk for damage to surrounding structures (blood vessels, bladder, gastrointestinal tract, and nervous structures). Importantly, the use of a linear insertion instrument or tool allows for greater application of torque to fixation screws.

Embodiments of the current doughnut-like implant can have a width of from about 20 millimeters to about 45 millimeters and a depth of from about 10 millimeters to about 30 millimeters. The heights for anterior curvatures of the present invention range from about 8 millimeters to about 25 millimeters and the heights for posterior curvatures of the current invention range from about 3 millimeters to about 20 millimeters.

Having disclosed the invention as required by Title 35 of the United States Code, Applicant now prays respectfully that Letters Patent be granted for his invention in accordance with the scope of the claims appended hereto.

What is claimed is:

1. A biocompatible metallic, plastic or combined metallic-plastic doughnut-like implant capable of frontal insertion between a superior and inferior lumbosacral vertebra, wherein said doughnut-like implant comprises a plurality of distinct generally upright load-supporting curvatures including load-bearing superior and inferior edges; said doughnut-like implant comprising:
   a) an asymmetrical central opening, including a central vertical axis, surrounded by said plurality of distinct generally upright load-supporting curvatures;
   b) an anterior load-supporting curvature protruding forward and away from said central vertical axis further comprising:
      i) one or more apertures located proximate said inferior edge for receiving one or more fasteners;
      ii) one or more windows allowing insertion of osteogenic, arthrodesis accelerating or other substances; and
      iii) a bore complementary to each said window and proximate said superior edge;
   c) a posterior load-supporting curvature angled more acutely than said anterior member;
   d) a first lateral load-supporting curvature intermediate between and connected with said anterior and said posterior load-supporting curvatures, wherein superior and inferior edges of said first lateral load-supporting curvature taper toward each other as said first lateral load-supporting-curvature traverses from said anterior load-supporting curvature to said posterior load-supporting curvature;
   e) a second lateral load-supporting curvature intermediate between and connected with said anterior and said posterior load-supporting curvatures, wherein superior and inferior edges of said second lateral load-supporting curvature taper toward each other as said second lateral load-supporting-curvature traverses from said anterior load-supporting curvature to said posterior load-supporting curvature;
   f) one or more detachable connectors associated with said one or more windows; each said detachable connector comprising:
      i) a first member including a hole for receiving a first fastener;
      ii) a second member capable of covering a majority of one of said windows for limiting outflow of said osteogenic, arthrodesis accelerating or other substances, wherein said second member comprises a hole for alignment with one of said bores and for receiving a second fastener; and
      iii) a transitional body connecting and offsetting said first member from said second member such that when said detachable connector is attached to said anterior load-supporting curvature said first member extends anterior to said anterior load-supporting curvature and superior to said anterior load-supporting curvature's superior edge; and
   g) a plurality of fasteners for use with said doughnut-like implant.

2. The invention of claim 1, wherein said transitional body is generally perpendicular to said first member and said second member.

3. The invention of claim 2, wherein said superior and inferior edges of said load-bearing curvatures are roughened.

4. The invention of claim 3, wherein said superior and inferior edges of said load-bearing curvatures are integral with each other.

5. The invention of claim 4 further comprising a porous coating applied to said superior and inferior edges of said load-bearing curvatures.

6. A biocompatible doughnut-like implant capable of frontal insertion between a superior and an inferior vertebra; said doughnut-like implant comprising:
   a) an asymmetrical opening comprising a reference generally vertical axis;
   b) distinct load-bearing curvatures, including superior and inferior edges, forming said asymmetrical opening; said distinct load-bearing curvatures comprising:
      i) a first load-bearing curvature protruding forward and away from said reference axis, wherein said first load-bearing curvature further comprises:
         A) one or more apertures located proximate said inferior edge for receiving one or more fasteners;
         B) one or more windows allowing insertion of osteogenic, arthrodesis accelerating or other substances; and
         C) a bore complementary to each said window and proximate said superior edge;
      ii) a second load-bearing curvature protruding toward said reference axis and angled more acutely than said first load-bearing curvature;
      iii) a third load-bearing curvature intermediate between and connected with said first load-bearing curvature and said second load-bearing curvature;
      iv) a fourth load-bearing curvature intermediate between and connected with said first load-bearing curvature and said second load-bearing curvature;
   c) a porous coating applied to one or more of said superior or inferior edges; and
   d) one or more detachable connectors associated with said one or more windows.

7. The invention of claim 6, wherein each said detachable connector further comprises:
   a) a first member including a hole for receiving a first fastener;
   b) a second member capable of covering a majority of one of said windows for limiting outflow of said osteogenic, arthrodesis accelerating or other substances, wherein said second member comprises a hole for alignment with one of said bores and for receiving a second fastener; and
   c) a transitional body connecting and offsetting said first member from said second member such that said when said detachable connector is attached to said anterior load-supporting curvature said first member extends anterior to said anterior load-supporting curvature and superior to said anterior load-supporting curvature's superior edge.

8. The invention of claim 7, wherein:
   a) said superior and inferior edges of said third load-bearing curvature taper toward each other as said third load-bearing curvature traverses from said first load-bearing curvature toward said second load-bearing curvature; and
   b) said superior and inferior edges of said fourth load-bearing curvature taper toward each other as said fourth load-bearing curvature traverses from said first load-bearing curvature toward said second load-bearing curvature.

9. The invention of claim 8, wherein said transitional body is generally perpendicular to said first member and said second member.

10. A biocompatible doughnut-like implant capable of frontal insertion between a superior and an inferior vertebra; said doughnut-like implant comprising an opening enclosed by a series of interconnected load-bearing generally upright sections including upper and lower edges and a detachable connector;
   to said series further comprising:
   a) an anterior section protruding forwardly; said anterior section further comprising:
      i) one or more apertures located proximate said inferior edge;
      ii) at least one window allowing insertion of osteogenic, arthrodesis accelerating or other substances; and
      iii) a bore complementary with and superior to each said window;
   b) a posterior section protruding forwardly and angled more acutely than said anterior section;
   c) first and second opposed lateral sections intermediate between and connected with said anterior and said posterior sections; and wherein
   said detachable connector is complementary with each said window; said detachable connector further comprising:
   a) a first member including a first hole; and
   b) a second member including a second hole.

11. The invention of claim 10, wherein:
   a) said posterior section comprises a protrusion angle of more than 30 degrees; and
   b) said anterior section comprises a protrusion angle of less than 30 degrees.

12. The invention of claim 11, wherein said edges of said sections of said series are roughened.

13. The invention of claim 12 further comprising a transitional body connecting and offsetting said first member from said second member such that said when said detachable connector is attached to said anterior section said first member extends anterior to said anterior section and superior to said anterior section's superior edge.

14. The invention of claim 13, wherein said first and said second lateral sections are tapered and protrude outwardly.

15. The invention of claim 14, wherein said second member is curved to follow a curvature of each said window.

16. The invention of claim 15 further comprising a porous coating applied to said edges.

17. The invention of claim 16, wherein:
   a) said upper and lower edges of said first lateral section taper toward each other as said first lateral section traverses from said anterior section toward said posterior section; and
   b) said upper and lower edges of said second lateral section taper toward each other as said second lateral section traverses from said anterior section toward said posterior section.

18. The invention of claim 17 wherein a screw can be inserted through said first member at an operating angle of from about 45 degrees to about 110 degrees.

19. A biocompatible doughnut-like implant capable of frontal insertion between a superior and an inferior vertebra; said doughnut-like implant comprising:
   a) an opening enclosed by a series of interconnected load-bearing sections including upper and lower edges; said series comprising:
      i) an anterior section protruding forwardly; said anterior section further comprising:

A) one or more apertures located proximate said inferior edge; and
B) one or more windows allowing insertion of osteogenic, arthrodesis accelerating or other substances;
ii) a posterior section protruding forwardly and angled more acutely than said anterior section; and
iii) first and second opposed lateral sections intermediate between and connected with said anterior and said posterior sections;
b) a detachable connector complementary with at least one of said windows; said detachable connector further comprising:
i) a first member including a first hole;
ii) a second member including:
A) a second hole; or
B) a keel; and
c) one or more fasteners for use with said biocompatible doughnut-like implant.

20. The invention of claim 19, wherein:
a) said posterior section comprises a protrusion angle of more than 30 degrees; and
b) said anterior section comprises a protrusion angle of less than 30 degrees.

21. The invention of claim 20 further comprising a transitional body connecting and offsetting said first member from said second member such that when said detachable connector is attached to said anterior section said first member extends anterior to said anterior section and superior to said anterior section's superior edge.

22. The invention of claim 21, wherein:
a) said upper and lower edges of said first lateral section taper toward each other as said first lateral section traverses from said anterior section toward said posterior section; and
b) said upper and lower edges of said second lateral section taper toward each other as said second lateral section traverses from said anterior section toward said posterior section.

23. The invention of claim 22 wherein a screw can be inserted through said first member at an operating angle of from about 45 degrees to about 110 degrees.

24. The invention of claim 23, wherein said anterior section comprises a generally flat area proximate said window, wherein said generally flat area is of greater surface area than said corresponding second member.

25. The invention of claim 24, wherein said second member is curved to follow a curvature of each said window.

26. A detachable connector for use with a biocompatible spinal implant; said detachable connector comprising:
a) a first member including a first hole for receiving a first fastener capable of securing said first member to bone;
b) a second member capable of impeding outflow of osteogenic, arthrodesis accelerating or other substances from said biocompatible spinal implant, wherein said second member comprises:
i) a second hole for receiving a second fastener capable securing said second member to said biocompatible spinal implant; or
ii) a keel capable of securing said second member to said biocompatible spinal implant; and
c) a transitional body connecting and offsetting said first member from said second member such that when said detachable connector is attached to said biocompatible spinal implant said first member extends anterior to said second member and superior to said biocompatible spinal implant.

27. The invention of claim 26, wherein said transitional body is generally perpendicular to said first member and said second member.

28. The invention of claim 27, wherein:
a) said first member includes an area that is relatively flat; and
b) said second member includes an area that is curved for aligning with a curvature of said biocompatible spinal implant.

29. The invention of claim 27, wherein:
a) said first member includes an area that is relatively flat; and
b) said second member includes an area that is relatively straight for aligning with a flattened area of said biocompatible spinal implant.

* * * * *